(12) United States Patent
Clavette et al.

(10) Patent No.: US 10,295,502 B2
(45) Date of Patent: May 21, 2019

(54) SYSTEMS FOR QUALITY MONITORING OF ADDITIVE MANUFACTURING

(71) Applicant: Delavan Inc, West Des Moines, IA (US)

(72) Inventors: Patrick L. Clavette, Simsbury, CT (US); Michael A. Klecka, Vernon, CT (US); Aaron T. Nardi, East Granby, CT (US); Greg C. Ojard, Vernon, CT (US)

(73) Assignee: Delavan Inc., West Des Moines, IA (US)

( * ) Notice: Subject to any disclaimer, the term of this patent is extended or adjusted under 35 U.S.C. 154(b) by 758 days.

(21) Appl. No.: 14/818,832

(22) Filed: Aug. 5, 2015

(65) Prior Publication Data

US 2017/0038342 A1   Feb. 9, 2017

(51) Int. Cl.
| | | |
|---|---|---|
| *G01N 29/14* | (2006.01) |
| *G01N 29/44* | (2006.01) |
| *G01N 29/04* | (2006.01) |
| *G01N 29/06* | (2006.01) |
| *B33Y 50/02* | (2015.01) |
| *B33Y 40/00* | (2015.01) |
| *C23C 24/04* | (2006.01) |

(Continued)

(52) U.S. Cl.
CPC ........... *G01N 29/14* (2013.01); *B29C 64/153* (2017.08); *B33Y 40/00* (2014.12); *B33Y 50/02* (2014.12); *C23C 24/04* (2013.01); *G01N 29/043* (2013.01); *G01N 29/0618* (2013.01); *G01N 29/4454* (2013.01); *B22F 3/008* (2013.01); *B22F 2999/00* (2013.01); *G01N 2291/0231* (2013.01); *G01N 2291/0251* (2013.01); *G05B 2219/37337* (2013.01); *G05B 2219/37351* (2013.01)

(58) Field of Classification Search
CPC .. G01N 29/14; G01N 29/043; G01N 29/0618; G01N 29/4454; G01N 2291/0231; G01N 2291/0251; G01N 2291/02854; G01N 2291/2697; B33Y 40/00; B33Y 50/02; B33Y 50/00; B22F 2/105; B22F 2003/1057; B29C 67/0077; G05B 2219/37337; G05B 2219/37351
USPC .......................... 73/587, 582, 588, 590, 579
See application file for complete search history.

(56) References Cited

U.S. PATENT DOCUMENTS

| | | |
|---|---|---|
| 4,024,522 A | 5/1977 | Clark et al. |
| 5,423,520 A | 6/1995 | Anderson et al. |
| 5,659,479 A | 8/1997 | Duley et al. |

(Continued)

OTHER PUBLICATIONS

Extended European Search Report dated Nov. 11, 2016, issued by the European Patent Office, in corresponding European Patent Application No. 16182176.4.

(Continued)

*Primary Examiner* — Lisa M Caputo
*Assistant Examiner* — Rose M Miller
(74) *Attorney, Agent, or Firm* — Locke Lord LLP; Daniel J. Fiorello; Scott D. Wofsy

(57) ABSTRACT

A system for quality monitoring of additive manufacturing includes an acoustic emission (AE) sensor configured to be attached to an additive manufacturing substrate and to output a sensor signal indicative of acoustic vibrations received at the AE sensor and an AE module. The AE module is configured to receive the sensor signal from the AE sensor and process the sensor signal to determine at least one characteristic of an additive manufacturing process and/or an additively manufactured article.

11 Claims, 5 Drawing Sheets

(51) Int. Cl.
*B29C 64/153* (2017.01)
*B22F 3/00* (2006.01)

(56) References Cited

U.S. PATENT DOCUMENTS

| | | |
|---|---|---|
| 6,065,342 A | 5/2000 | Kerr et al. |
| 6,553,275 B1 | 4/2003 | Mazumder |
| 6,580,959 B1 | 6/2003 | Mazumder |
| 6,925,346 B1 | 8/2005 | Mazumder et al. |
| 8,629,368 B2 | 1/2014 | Mazumder et al. |
| 2014/0007692 A1 | 1/2014 | Hines |
| 2015/0024233 A1 | 1/2015 | Gunther |
| 2016/0185048 A1 | 6/2016 | Dave et al. |

OTHER PUBLICATIONS

Invitation pursuant to Article 94(3) and Rule 71(1) EPC dated Sep. 20, 2017, issued by the European Patent Office, in the corresponding European Patent Application No. 16182176.4.

SYSTEMS FOR QUALITY MONITORING OF ADDITIVE MANUFACTURING

BACKGROUND

1. Field

The present disclosure relates to additive manufacturing, more specifically to quality monitoring for additive manufacturing.

2. Description of Related Art

Additive Manufacturing (AM) processes are continuing to become more ubiquitous, however, traditional inspection processes are a limitation in manufacturing rate and/or quality. Traditional inspection processes require post manufacturing inspection which can be at least partially destructive to the additively manufactured article. Such processes are time consuming and expensive.

Such conventional methods and systems have generally been considered satisfactory for their intended purpose. However, there is still a need in the art for improved quality monitoring systems for additive manufacturing. The present disclosure provides a solution for this need.

SUMMARY

In accordance with at least one aspect of this disclosure, a system for quality monitoring of additive manufacturing includes an acoustic emission (AE) sensor configured to be attached to an additive manufacturing substrate and to output a sensor signal indicative of acoustic vibrations received at the AE sensor. The system also includes an AE module that is configured to receive the sensor signal from the AE sensor and process the sensor signal to determine at least one characteristic of an additive manufacturing process and/or an additively manufactured article. The system can include at least one additional AE sensor operatively connected to the AM module.

The AE module can be configured to receive the sensor signal in real time during the additive manufacturing process. The AE module can be configured to process the sensor signal in real time.

The at least one characteristic of the additively manufactured article can include coat delamination, coat cracking, or coat material quality. The coat material quality can include at least one of coat particle size or composition.

The at least one characteristic of the additive manufacturing process can include an amount and/or a quality of at least one of a powder supply or an injection gas supply.

The system can include a spray controller operatively connected to the AE module to receive AE module data from the AE module. The spray controller can be configured to be operatively connected to at least one of a sprayer, a powder supply, or an injection gas supply to control a powder spray onto the substrate.

The AE module data can include computer executable instruction for the spray controller to start, stop, and/or otherwise modify the powder spray based on the at least one characteristic of an additive manufacturing process and/or an additively manufactured article.

In accordance with at least one aspect of this disclosure, a method for monitoring a quality of additive manufacturing can include receiving a sensor signal from an acoustic emissions (AE) sensor, and processing the sensor signal to determine at least one characteristic of an additive manufacturing process and/or an additively manufactured article. The method can include receiving a sensor signal from at least one additional AE sensor.

Receiving the sensor signal can include receiving the sensor signal in real time during the additive manufacturing process. Processing the sensor signal can include processing the sensor signal in real time.

The method can include outputting data to a spray controller, wherein the spray controller is configured to be operatively connected to at least one of a sprayer, a powder supply, or an injection gas supply to control a powder spray onto the substrate. Outputting data can include instructing the spray controller to start, stop, and/or otherwise modify the powder spray based on the at least one characteristic of an additive manufacturing process and/or an additively manufactured article.

These and other features of the systems and methods of the subject disclosure will become more readily apparent to those skilled in the art from the following detailed description taken in conjunction with the drawings.

BRIEF DESCRIPTION OF THE DRAWINGS

So that those skilled in the art to which the subject disclosure appertains will readily understand how to make and use the devices and methods of the subject disclosure without undue experimentation, embodiments thereof will be described in detail herein below with reference to certain figures, wherein.

DETAILED DESCRIPTION

Figure 1:
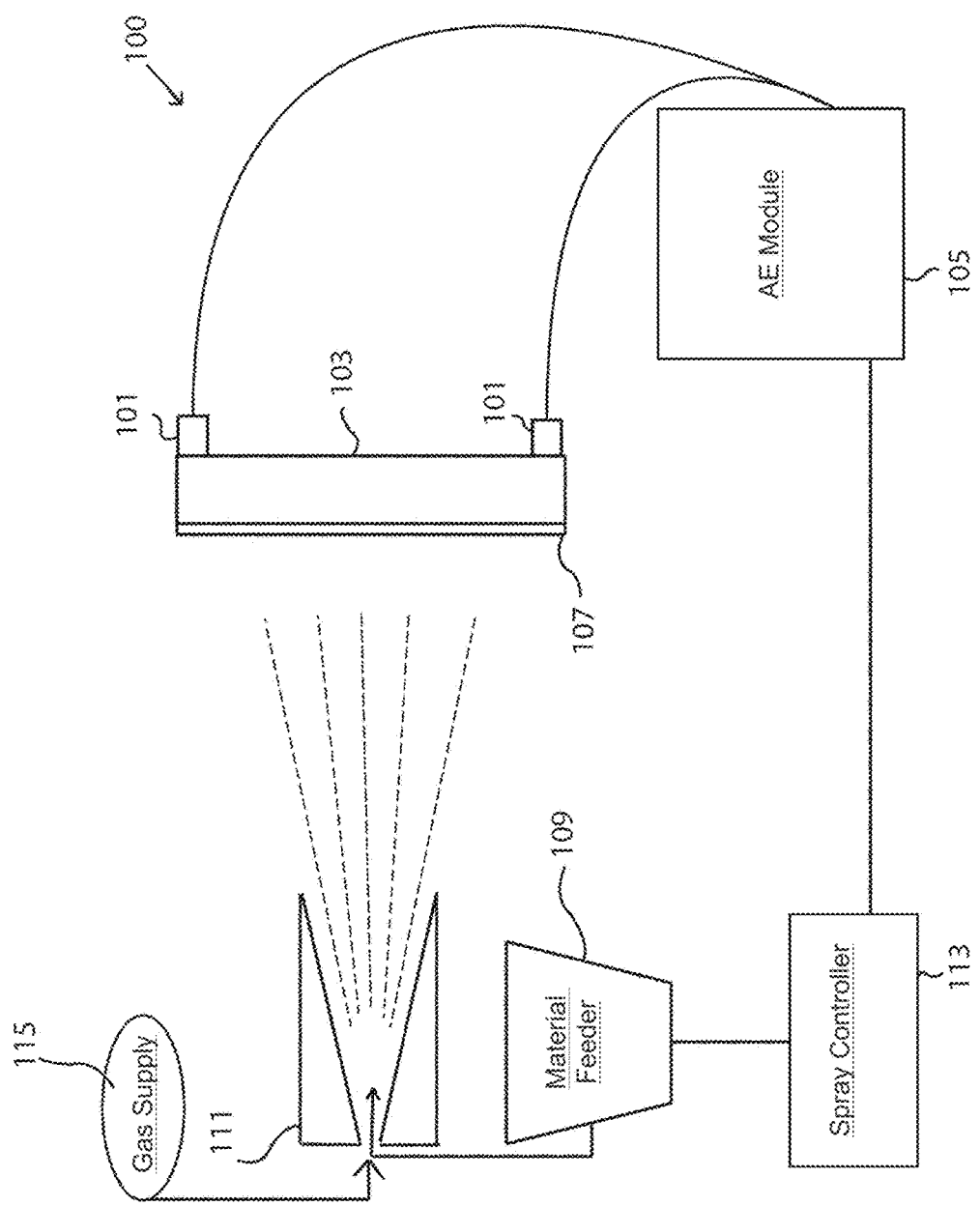
FIG. 1 is a schematic view of a system in accordance with this disclosure, showing acoustic emissions sensors connected to a substrate.

Reference will now be made to the drawings wherein like reference numerals identify similar structural features or aspects of the subject disclosure. For purposes of explanation and illustration, and not limitation, an illustrative view of an embodiment of a system in accordance with the disclosure is shown in FIG. 1 and is designated generally by reference character 100. The systems and methods described herein can be used to monitor and/or control an additive manufacturing quality (e.g., quality of process or product) in any suitable manner (e.g., in real time).

In accordance with at least one aspect of this disclosure, a system 100 for quality monitoring of additive manufacturing includes an acoustic emission (AE) sensor 101 configured to be attached to an additive manufacturing substrate 103 and to output a sensor signal indicative of acoustic vibrations received at the AE sensor 101. As shown, the system 100 can include at least one additional AE sensor 101 operatively connected to the AE module 105. Any suitable number and/or positions of AE sensors 101 are contemplated herein.

The system 100 also includes an AE module 105 that is configured to receive the sensor signal from the AE sensor 101 and process the sensor signal to determine at least one characteristic of an additive manufacturing process and/or an additively manufactured article (e.g., substrate 103 with coating 107). The AE module 105 can include any suitable hardware (e.g., a microprocessor, memory, etc.) and/or software configured to receive sensor signals from the AE sensors 101 and process the sensor signals.

Figure 2:
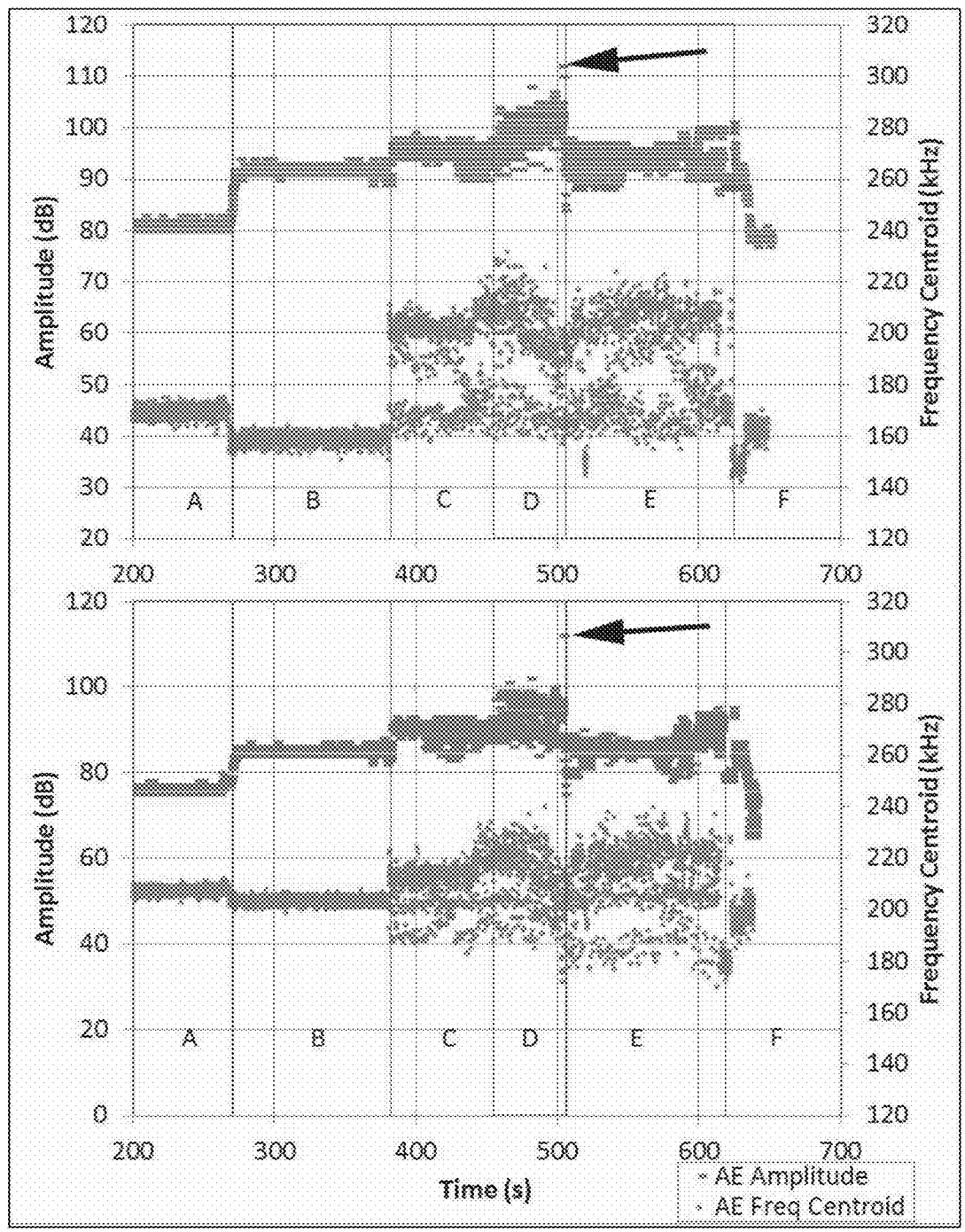
FIG. 2 illustrates vibrational received signal using an embodiment of a system in accordance with this disclosure, shown including phenomena periods A-F. AE for 90Ta-10W sprayed on mild steel. Top plot is the WD sensor, bottom is the µ30 sensor. Phenomena periods A-F correspond to following A) nitrogen purge, B) helium purge, C) powder deposition with low amplitude AE, D) powder deposition with higher amplitude AE (delaminating at the end of this period as shown by the arrow), E) post-delamination powder deposition, F) movement of the nozzle away from the surface and conclusion of the test.
Figure 3:
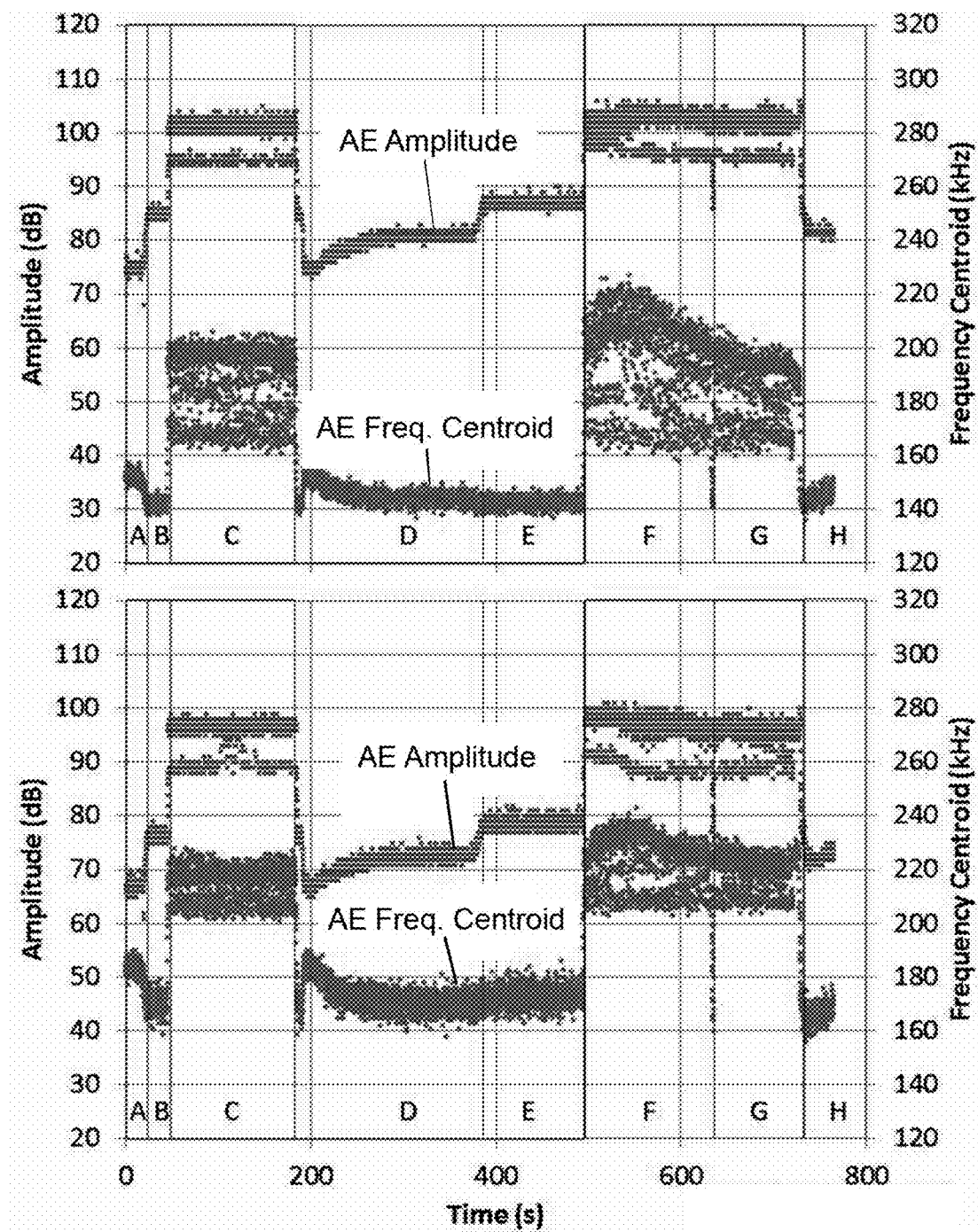
FIG. 3 illustrates vibrational received signal using an embodiment of a system in accordance with this disclosure, shown including phenomena periods A-H. AE for 90Ta-10W sprayed on aluminum. Top plot is the WD sensor, bottom is the µ30 sensor. Phenomena periods A-H correspond to the following: A) nitrogen purge, B) helium purge, C) powder deposition using cold He with fairly high amplitude AE, D) movement of the nozzle away from the surface followed by switching from helium to nitrogen and addition of another 50 grams of powder, E) helium purge in preparation for second run, F) second powder deposition with hot He, G) a third powder deposition (hot He) period with no inter-layer purges, H) movement of the nozzle away from the surface from the surface and conclusion of the test.
Figure 4:
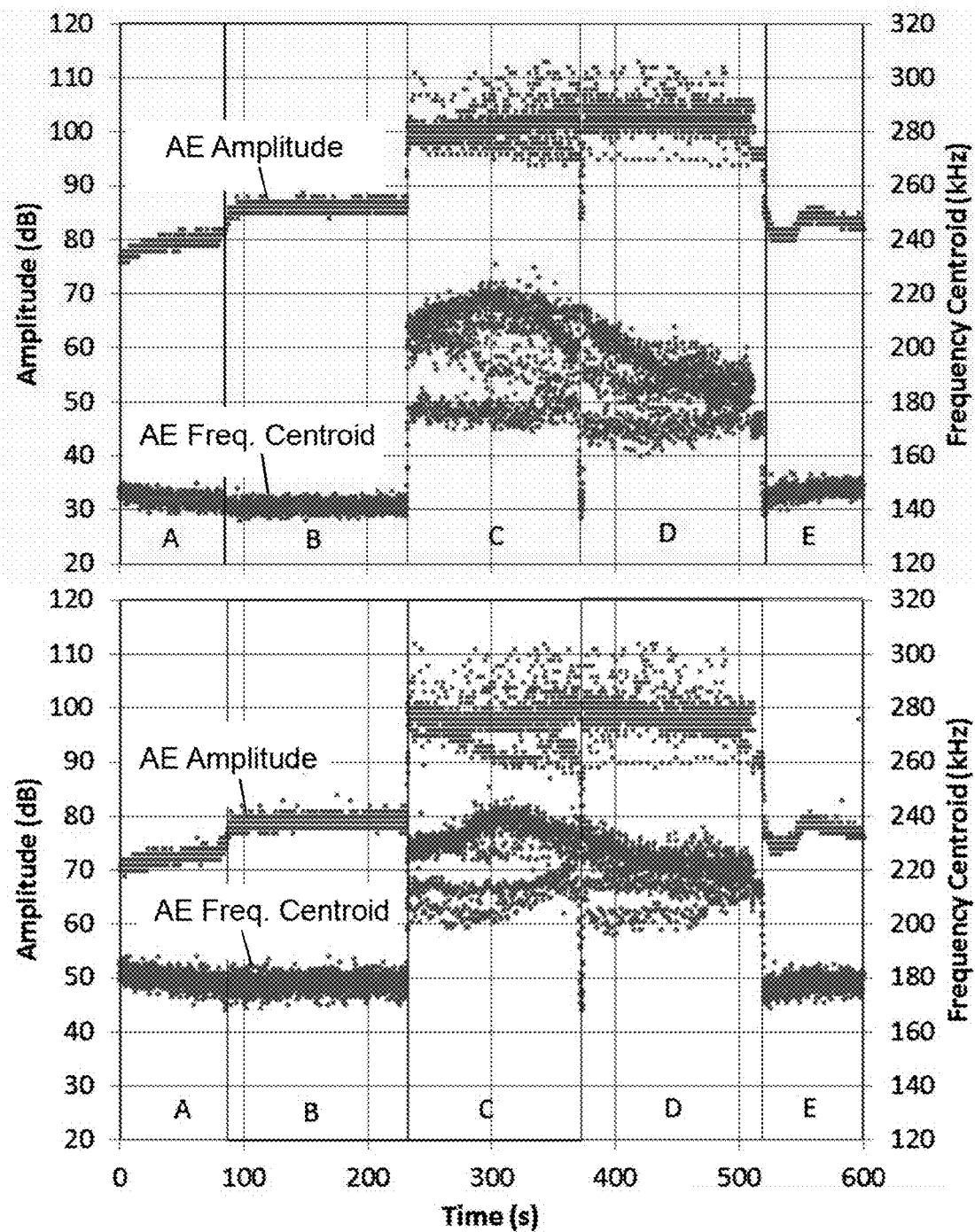
FIG. 4 illustrates vibrational received signal using an embodiment of a system in accordance with this disclosure, shown including phenomena periods A-E. AE for 90Ta-10W containing large agglomerates sprayed on aluminum. Top plot is the WD sensor, bottom is the µ30 sensor. Phenomena periods A-E correspond to the following: A) nitrogen purge, B) helium purge, C) powder deposition with fairly high amplitude AE, D) a second period of powder deposition, and E) movement of the nozzle away from the surface and conclusion of the test.
Figure 5:
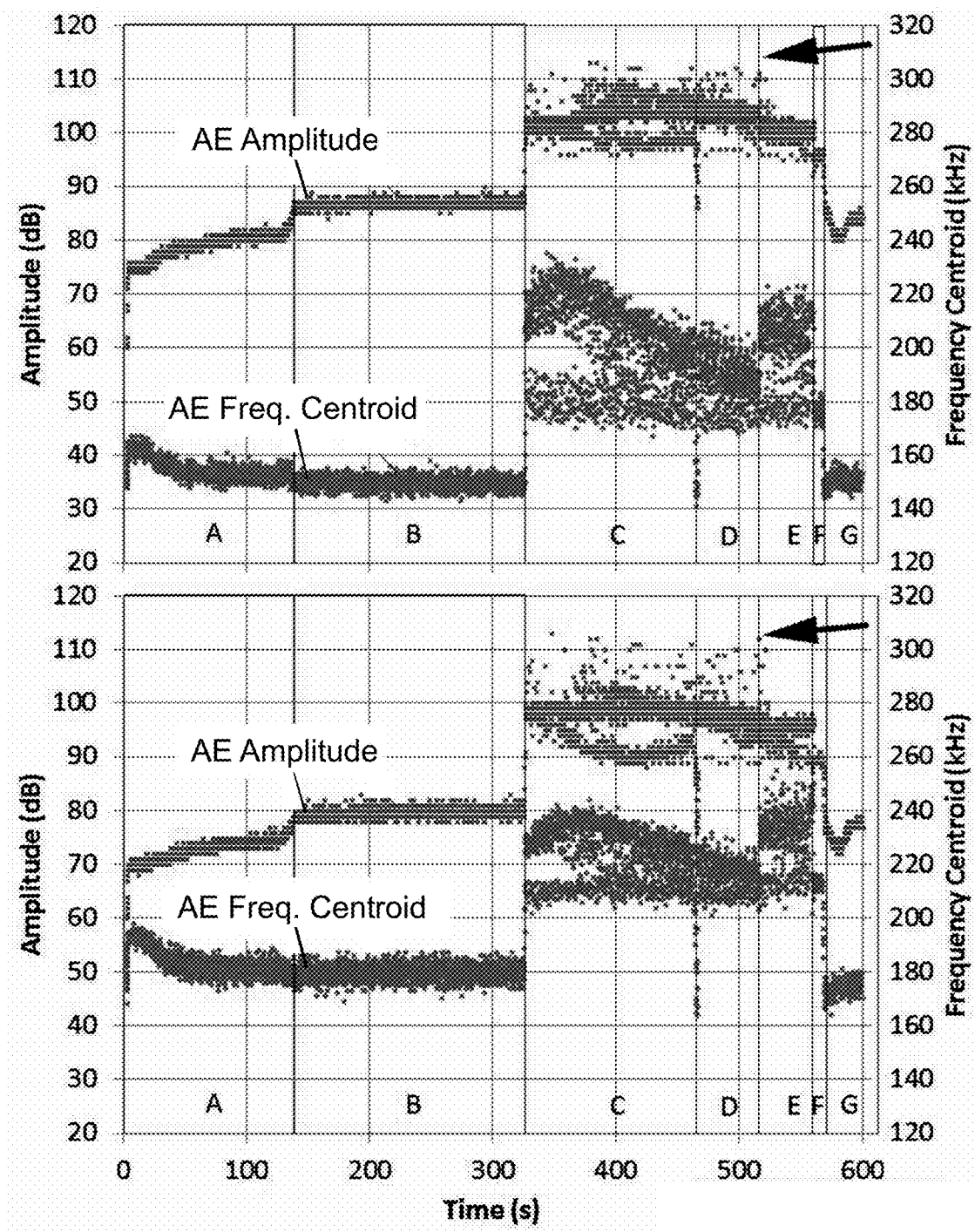
FIG. 5 illustrates vibrational signal received using an embodiment of a system in accordance with this disclosure, shown including phenomena periods A-G. AE for 90Ta- 10W containing large agglomerates sprayed on aluminum, where a delamination occurred. Top plot is the WD sensor, bottom is the μ30 sensor. Phenomena periods correspond to the following: A) nitrogen purge, B) helium purge, C) powder deposition with fairly high amplitude AE, D) a second period of powder deposition leading up to delamination as shown by the arrow, and E) a period of poor coating (there were small fragments spalling from the deposit) leading up to the powder running out, F) a period when the nozzle was still making passes on the substrate with no powder in the hopper, and G) movement of the nozzle away from the surface and conclusion of the test.

To process the signals, for example, The AE module 105 can plot and/or correlate certain patterns of vibration to certain phenomena associated with the vibrations received through the substrate 103. In certain embodiments, the AE module 105 can display the vibration data for a user to manually correlate the data with certain phenomena. Referring to FIG. 2-4, some experimentally determined correlations are shown as examples.

The AE module 105 can be configured to receive the sensor signal in real time during the additive manufacturing process or at any other suitable time (e.g., after additive manufacturing or at any suitable intervals during additive manufacturing). The AE module 105 can be configured process the sensor signal in real time or at any other suitable time(s) (e.g., after additive manufacturing or at any suitable interval(s) during additive manufacturing).

The at least one characteristic of the additively manufactured article can include coat delamination, coat cracking, or coat material quality (e.g., of cold powder coat 107). In certain embodiments, the coat material quality can include at least one of coat particle size or composition.

The at least one characteristic of the additive manufacturing process can include an amount and/or a quality of at least one of a powder supply (e.g., from material feeder 109). In certain embodiments, the at least one characteristic of the additive manufacturing process can additionally or alternatively include an injection gas supply 115 (e.g., pressure, flow rate, or any other suitable characteristic of gas flowing from a gas source to spray powder from the material feeder 109 through sprayer 111).

The system 100 can include a spray controller 113 operatively connected to the AE module 105 to receive AE module data from the AE module 105. The spray controller 113 can be operatively connected to the AE module in any suitable manner (e.g., wireless, wired). In certain embodiments, the AE module 105 and the spray controller 113 can be embodied together on a single device (e.g., a computer, a software package, and/or any other suitable hardware or software). The spray controller 113 can be configured to be operatively connected to at least one of the sprayer 111, a powder supply (e.g., from material feeder 109), or an injection gas supply 115 (e.g., operatively connected to the sprayer 111) to control a powder spray onto the substrate 103.

In certain embodiments, the AE module data can include computer executable instruction for the spray controller 113 to start, stop, and/or otherwise modify the powder spray based on the at least one characteristic of an additive manufacturing process and/or an additively manufactured article. For example, if the AE module 105 determines that there is no powder spraying or if there is not suitable gas available from gas supply 115, the AE module 105 can instruct the spray controller 113 to modify and/or stop spraying and abort the manufacturing process. If the AE module 105 determines that the quality of the powder is incorrect for the desired coating 107, and/or that cracks are forming in the coating 107, and/or if delamination of the coating 107 is occurring, the AE module 105 can instruct the spray controller 113 to modify and/or stop spraying to prevent a finished product with undesired quality. It is contemplated that the AE suitable module data can include any other suitable data as is appreciated by those skilled in the art.

In accordance with at least one aspect of this disclosure, a method for monitoring a quality of additive manufacturing can include receiving a sensor signal from an acoustic emissions (AE) sensor (e.g., sensors 101), and processing the sensor signal to determine at least one characteristic of an additive manufacturing process and/or an additively manufactured article. The method can include receiving a sensor signal from at least one additional AE sensor (e.g., sensor 101).

Receiving the sensor signal can include receiving the sensor signal in real time during the additive manufacturing process. Processing the sensor signal can include processing the sensor signal in real time.

The method can include outputting data to a spray controller (e.g., spray controller 113), wherein the spray controller is configured to be operatively connected to at least one of a sprayer, a powder supply, or an injection gas supply 115 to control a powder spray onto the substrate. Outputting data can include instructing the spray controller to start, stop, and/or otherwise modify the powder spray based on the at least one characteristic of an additive manufacturing process and/or an additively manufactured article. The methods as described herein can be implemented via any suitable manner (e.g., suitable computer executable code, analog hardware, or any other suitable hardware or software).

As described above, the system 100 can detect changes in the signal parameters and allow a non-destructive means to evaluate coating quality. Powder problems, coating cracking, delamination can be detected real time and a feedback signal can be provided to the cold sprayer (e.g., to shut of the flow and prevent the waste of expensive feedstock powder and/or helium gas).

The methods and systems of the present disclosure, as described above and shown in the drawings, provide for additive manufacturing systems with superior properties including quality monitoring. While the apparatus and methods of the subject disclosure have been shown and described with reference to embodiments, those skilled in the art will readily appreciate that changes and/or modifications may be made thereto without departing from the spirit and scope of the subject disclosure.

What is claimed is:

1. A system for quality monitoring of cold spray additive manufacturing, comprising:
   a cold spray acoustic emission (AE) sensor configured to be attached to an additive manufacturing substrate and to output a sensor signal indicative of acoustic vibrations received at the AE sensor; and
   a cold spray AE module configured to:
   receive the sensor signal from the AE sensor; and
   process the sensor signal to determine at least one characteristic of an additive manufacturing process and/or an additively manufactured article.

2. The system of claim 1, further comprising at least one additional AE sensor disposed on the substrate and operatively connected to the AE module.

3. The system of claim 1, wherein the AE module is configured to receive the sensor signal in real time during the additive manufacturing process.

4. The system of claim 1, wherein the AE module is configured to process the sensor signal in real time.

5. The system of claim 1, further comprising a spray controller operatively connected to the AE module to receive AE module data from the AE module, wherein the spray controller is configured to be operatively connected to at least one of a sprayer, a powder supply, or an injection gas supply to control a powder spray onto the substrate.

6. The system of claim 5, wherein the AE module data includes computer executable instruction for the spray controller to at least one of start, stop, or otherwise modify the powder spray based on the at least one characteristic of an additive manufacturing process or an additively manufactured article, or any combination thereof.

7. A method for monitoring a quality of cold spray additive manufacturing, comprising:
   receiving a sensor signal from a cold spray acoustic emissions (AE) sensor disposed on an additive manufacturing substrate; and
   processing the sensor signal to determine at least one characteristic of a cold spray additive manufacturing process or a cold spray additively manufactured article, or any combination thereof.

8. The method of claim 7, wherein receiving the sensor signal includes receiving the sensor signal in real time during the additive manufacturing process.

9. The method of claim 7, wherein processing the sensor signal includes processing the sensor signal in real time.

10. The method of claim 7, further comprising outputting data to a spray controller, wherein the spray controller is configured to be operatively connected to at least one of a sprayer, a powder supply, or an injection gas supply to control a powder spray onto the substrate.

11. The method of claim 10, wherein outputting data includes instructing the spray controller to at least one of start, stop, or otherwise modify the powder spray based on the at least one characteristic of an additive manufacturing process or an additively manufactured article, or any combination thereof.

* * * * *